US010299740B2

(12) United States Patent
Mc Carthy et al.

(10) Patent No.: US 10,299,740 B2
(45) Date of Patent: May 28, 2019

(54) METHODS AND SYSTEMS FOR CONE-BEAM COMPUTED TOMOGRAPHY

(71) Applicant: General Electric Company, Schenectady, NY (US)

(72) Inventors: Thomas Mc Carthy, Paris (FR); Yves Lucien Trousset, Palaiseau (FR)

(73) Assignee: General Electric Company, Schenectady, NY (US)

( * ) Notice: Subject to any disclaimer, the term of this patent is extended or adjusted under 35 U.S.C. 154(b) by 312 days.

(21) Appl. No.: 14/869,838

(22) Filed: Sep. 29, 2015

(65) Prior Publication Data

US 2017/0086758 A1    Mar. 30, 2017

(51) Int. Cl.
| | |
|---|---|
| A61B 6/00 | (2006.01) |
| A61B 6/03 | (2006.01) |
| A61B 6/04 | (2006.01) |
| A61B 6/10 | (2006.01) |

(52) U.S. Cl.
CPC .............. *A61B 6/102* (2013.01); *A61B 6/032* (2013.01); *A61B 6/035* (2013.01); *A61B 6/10* (2013.01); *A61B 6/4085* (2013.01); *A61B 6/4435* (2013.01); *A61B 6/4441* (2013.01); *A61B 6/488* (2013.01); *A61B 6/542* (2013.01); *A61B 6/545* (2013.01); *A61B 6/547* (2013.01)

(58) Field of Classification Search
CPC ......... A61B 6/032; A61B 6/035; A61B 6/102; A61B 6/4085; A61B 6/4435; A61B 6/4441; A61B 6/488; A61B 6/542; A61B 6/545; A61B 6/547
USPC ..................................... 378/196–197, 62, 91
See application file for complete search history.

(56) References Cited

U.S. PATENT DOCUMENTS

| | | | | |
|---|---|---|---|---|
| 3,720,817 A | * | 3/1973 | Dinwiddie ............. | A61B 6/102 600/1 |
| 4,578,757 A | | 3/1986 | Stark | |
| 5,485,502 A | * | 1/1996 | Hinton .................. | A61B 6/102 250/363.01 |
| 5,878,112 A | * | 3/1999 | Koertge .................... | F16P 3/12 378/209 |
| 6,272,368 B1 | * | 8/2001 | Alexandrescu .......... | A61B 6/08 250/349 |
| 6,424,731 B1 | * | 7/2002 | Launay .................. | A61B 6/032 382/128 |
| 6,735,280 B2 | * | 5/2004 | Horbaschek ........... | A61B 6/102 378/205 |
| 6,814,490 B1 | * | 11/2004 | Suhm ................... | A61B 6/4405 378/195 |

(Continued)

OTHER PUBLICATIONS

International Search Report and Written Opinion for corresponding PCT application No. PCT/US2016/043824 dated Jan. 13, 2017; 15 pages.

*Primary Examiner* — Allen C. Ho
(74) *Attorney, Agent, or Firm* — McCoy Russell LLP

(57) ABSTRACT

Various methods and systems are provided for collision avoidance in cone-beam computed tomography (CT) systems. In one embodiment, a method for an imaging apparatus comprises calculating a likelihood of a collision between the imaging apparatus and a subject and/or its support based on a model of the subject, performing a scan of the subject responsive to the likelihood below a threshold, and not performing the scan otherwise. In this way, collisions between the patient and the imaging apparatus can be avoided.

20 Claims, 6 Drawing Sheets

(56) References Cited

U.S. PATENT DOCUMENTS

| | | | | |
|---|---|---|---|---|
| 6,830,375 B2* | 12/2004 | Deshpande | A61B 6/105 | 378/197 |
| 6,940,685 B2* | 9/2005 | Chrappan Soldavini | H02P 25/034 | 318/560 |
| 6,985,556 B2* | 1/2006 | Shanmugavel | A61B 6/102 | 250/363.02 |
| 7,029,175 B2* | 4/2006 | Karaus | A61B 6/102 | 378/197 |
| 7,034,492 B2* | 4/2006 | Curtis | A61B 6/102 | 318/560 |
| 7,130,378 B2* | 10/2006 | Akutsu | A61B 6/10 | 378/117 |
| 7,354,196 B2* | 4/2008 | Boese | A61B 6/032 | 378/189 |
| 7,379,533 B2* | 5/2008 | Koertge | A61B 6/102 | 378/117 |
| 7,428,296 B2* | 9/2008 | Bernhardt | A61B 6/102 | 378/117 |
| 7,455,453 B2* | 11/2008 | Lauritsch | A61B 6/102 | 378/195 |
| 7,564,949 B2* | 7/2009 | Sattler | A61B 6/102 | 378/117 |
| 7,609,813 B2* | 10/2009 | Curtis | A61B 6/102 | 318/560 |
| 7,855,656 B2* | 12/2010 | Maschke | A61B 6/102 | 340/573.1 |
| 7,857,512 B2* | 12/2010 | Camus | A61B 6/102 | 378/196 |
| 8,262,554 B2* | 9/2012 | Sayeh | A61B 6/032 | 378/65 |
| 8,269,178 B2* | 9/2012 | Blom | G01D 5/24 | 250/363.03 |
| 8,529,128 B2* | 9/2013 | Horiuchi | A61B 6/4482 | 378/196 |
| 8,660,694 B2* | 2/2014 | Lurz | A61B 6/4441 | 700/255 |
| 8,755,492 B2* | 6/2014 | Lee | H05G 1/02 | 378/115 |
| 8,824,633 B2* | 9/2014 | Ohishi | A61B 6/4014 | 378/92 |
| 8,848,874 B2* | 9/2014 | Kargar | A61B 6/102 | 378/117 |
| 9,125,286 B2* | 9/2015 | De Man | H05G 1/28 | |
| 9,259,282 B2* | 2/2016 | Azizian | A61B 19/2203 | |
| 9,326,702 B2* | 5/2016 | Eichler | A61B 6/102 | |
| 9,348,337 B2* | 5/2016 | Chen | A61B 6/102 | |
| 9,486,647 B2* | 11/2016 | Bergfjord | A61N 5/1048 | |
| 9,526,462 B2* | 12/2016 | Narabu | A61B 6/0407 | |
| 9,766,072 B2* | 9/2017 | Kim | B62D 15/0295 | |
| 9,892,233 B2* | 2/2018 | Zeilinger | A61B 6/467 | |
| 10,076,295 B2* | 9/2018 | Gemmel | A61B 6/4441 | |
| 2006/0274888 A1 | 12/2006 | Bernhardt et al. | | |
| 2008/0162046 A1* | 7/2008 | Kotian | A61B 6/547 | 701/300 |
| 2011/0208034 A1* | 8/2011 | Heid | G01S 13/06 | 600/407 |
| 2011/0224904 A1 | 9/2011 | Feiten et al. | | |
| 2013/0345543 A1* | 12/2013 | Steibel, Jr. | A61B 6/467 | 600/407 |
| 2014/0185751 A1 | 7/2014 | De Man et al. | | |
| 2015/0046137 A1* | 2/2015 | Zeilinger | A61B 6/467 | 703/2 |
| 2015/0190204 A1 | 7/2015 | Popovi | | |

* cited by examiner

METHODS AND SYSTEMS FOR CONE-BEAM COMPUTED TOMOGRAPHY

FIELD

Embodiments of the subject matter disclosed herein relate to non-invasive imaging, and more particularly, to collision avoidance in cone beam computed tomography imaging systems.

BACKGROUND

In cone-beam computed tomography (CT) systems, an x-ray source and an x-ray detector are generally mounted on opposing ends of a substantially C-shaped gantry such that x-rays emitted by the source in a cone-shaped beam are incident on and detectable by the x-ray detector. The source and the detector are positioned such that when an object (e.g., a human extremity) is interposed there between and is irradiated with x-rays, the detector produces data representative of characteristics of the interposed object. The data produced is typically displayed on a monitor or electronically stored.

The C-arm gantry defines an axis of rotation about which the source and detector are rotatable. By positioning this axis of rotation at or near an object, and by rotating the source and detector around the object in an orbital motion, images of the object taken at a plurality of different orientations can be obtained. These images can be combined to generate a comprehensive three-dimensional image of the object, for example using methods of image reconstruction.

Such CT system configurations typically have a small field of view and thus can only image a small portion of an object during a single scan. When imaging an off-center portion of an object, say a liver of a patient, the table upon which the patient rests during the scan is typically positioned such that the anatomy of interest coincides with the field of view. However, it is possible that the detector and/or the source may collide with the patient because the patient is now positioned closer to the trajectories of the detector and the source. Currently, imaging system operators use a trial-and-error approach wherein the patient is repositioned so that no such collisions occur. In some instances, repositioning the patient may lead to the anatomy of interest lying outside of the imaging field of view. If the patient is imaged in these instances, then the patient needlessly receives radiation dose because the anatomy of interest is not actually imaged. Typically, finding the optimal position of the subject where no collisions occur and the anatomy of interest is successfully imaged can take up to fifteen minutes of time.

BRIEF DESCRIPTION

In one embodiment, a method for an imaging apparatus comprises calculating a likelihood of a collision between the imaging apparatus and a subject based on a model of the subject, performing a scan of the subject responsive to the likelihood below a threshold, and not performing the scan otherwise. In this way, exposure of a patient to radiation dose can be minimized. Furthermore, collisions between the patient and the imaging apparatus can be avoided.

It should be understood that the brief description above is provided to introduce in simplified form a selection of concepts that are further described in the detailed description. It is not meant to identify key or essential features of the claimed subject matter, the scope of which is uniquely defined by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 4:
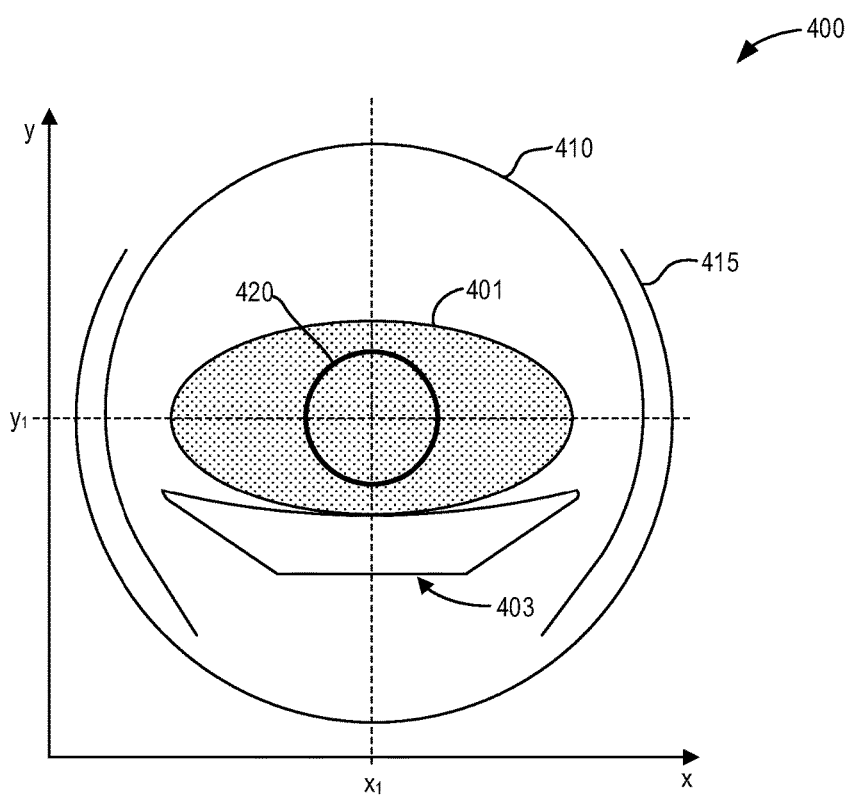
FIG. 4 shows a diagrammatical view of source and detector trajectories with respect to a subject centered in an imaging plane.
Figure 5:
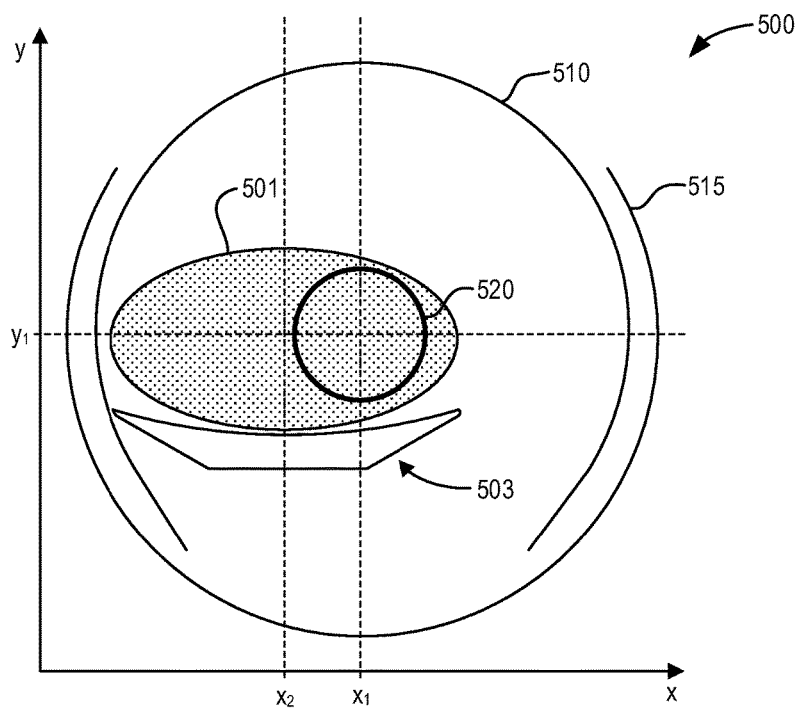
FIG. 5 shows a diagrammatical view of source and detector trajectories with respect to a subject positioned off-center in an imaging plane with no expected collision.
Figure 6:
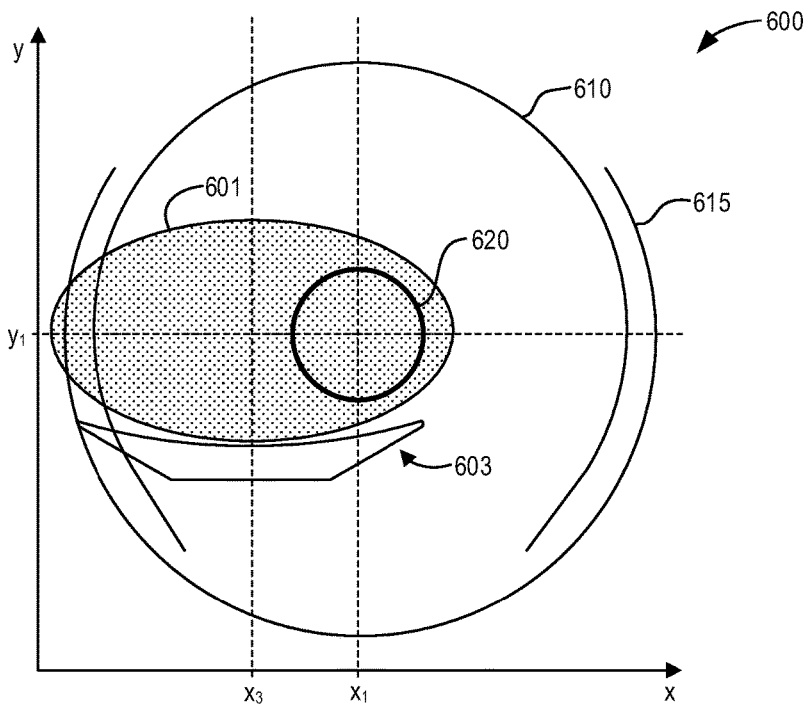
FIG. 6 shows a diagrammatical view of source and detector trajectories with respect to a subject positioned off-center in an imaging plane with an expected collision.

The following description relates to various embodiments of medical imaging systems. In particular, methods and systems are provided for collision avoidance in a computed tomography (CT) imaging system. An example of a CT imaging system that may be used to acquire images processed in accordance with the present techniques is provided in FIG. 1. Though a CT system is described by way of example, it should be understood that the present techniques may also be useful when applied to images acquired using other imaging modalities, such as tomosynthesis, MRI, PET, SPECT, C-arm angiography, mammography ultrasound, and so forth. The present discussion of a CT imaging modality is provided merely as an example of one suitable imaging modality. For example, a CT system in a C-arm configuration, such as the system depicted in FIG. 2, includes a source and a detector mounted opposite to each other on the ends of a substantially C-shaped or semi-circular gantry, or C-arm, thereby defining an imaging plane with an isocenter. During an image acquisition, the C-arm may rotate the source and the detector about an axis of rotation, which may coincide with the isocenter. Typically, a subject to be imaged, such as a patient, is positioned within the imaging plane such that radiation generated by the source passes through the subject and is detected by the detector. For cone beam CT, the field of view (FOV) of the imaging system is small and centered on the isocenter. In some instances, the region of interest (ROI) to be imaged may be off-center with respect to the subject, and so the subject should be positioned such that the FOV coincides with the ROI. However, when the subject is off-center, collisions between the imaging assembly and the subject are possible. A method for avoiding such collisions, such as the method shown in FIG. 3, may include determining an optimal position of a subject to image the ROI. The ROI may be detected from a prior reconstruction (organ segmentation in CT) or from a look up table depending on the "anatomy" that the operator indicates potentially adjusted with patient size/height/weight, for example. In some examples, the optimal position of the subject may be determined based on information such as the weight and height of the subject. In some more examples, a CT scan where the whole body section is covered by the image may provide information to determine and/or approximate the boundaries of the patient (skin). This may also be obtained using several partial body scans (tomographic or fluoroscopic), for example. In other examples, a prior scan may be obtained wherein the subject is centered on the isocenter, as shown in FIG. 4, in order to determine the shape and size of the subject. After determining the optimal location of the subject to image the off-center ROI, the method may further include determining if a collision between the imaging system and the subject will occur. If a collision will not occur, for example as shown in FIG. 5, then a diagnostic scan or scan may be performed. In addition, the patient bed and/or the imaging gantry may be automatically positioned at the desired position, for example. However, if a collision will occur, for example as shown in FIG. 6, then an operator of the imaging system may be notified so that the collision may be avoided.

Figure 1:
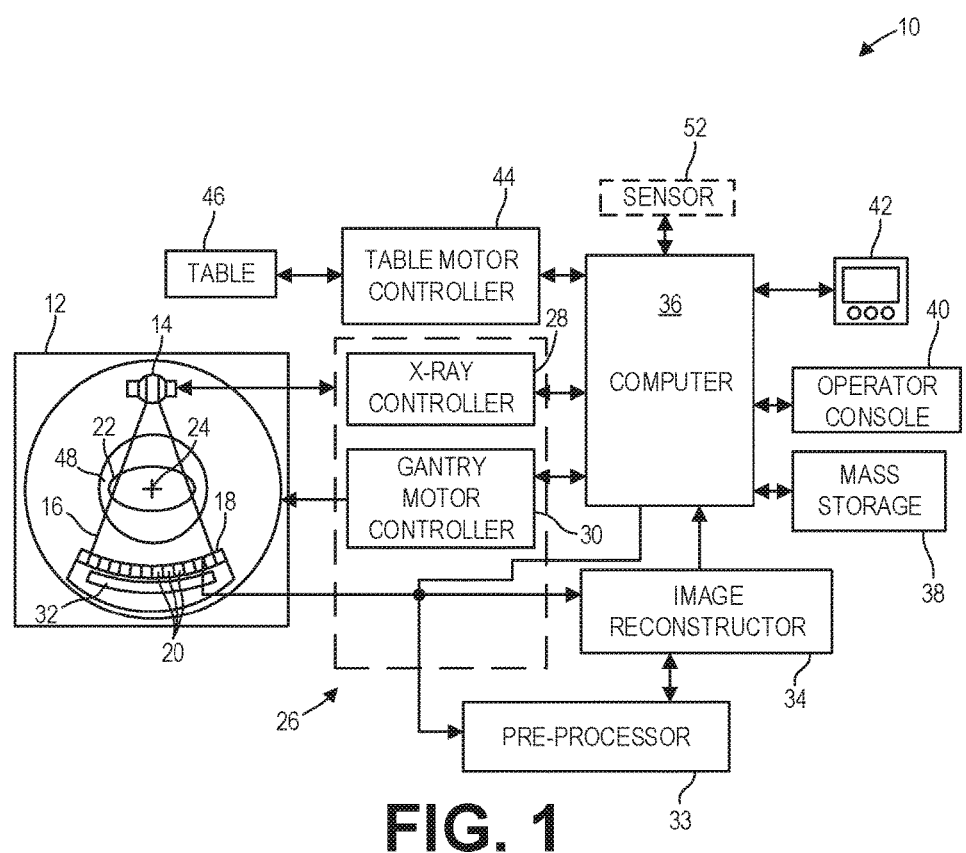
FIG. 1 is a block schematic diagram of an exemplary imaging system according to an embodiment of the invention.

Referring to FIG. 1, a CT imaging system 10 is shown as including a gantry 12. In some examples, CT imaging system 10 may be an energy integrating, a photon counting (PC), or a photon energy discriminating (ED) CT detector system. Gantry 12 includes an x-ray source 14 that projects a beam of x-rays 16 toward detector array 18. The x-rays pass through a subject 22, such as a patient, to generate attenuated x-rays. In an alternative embodiment, each detector element 20 of detector array 18 may be a photon energy integrating detector, a photon counting detector, or a photon energy discriminating detector. Each detector element 20 produces an electrical signal that represents an intensity of the attenuated x-rays. During a scan to acquire projection data, gantry 12 and components mounted on gantry 12 rotate about a center of rotation 24.

Rotation of a gantry 12 and an operation of x-ray source 14 are governed by a control mechanism 26 of CT imaging system 10. Control mechanism 26 includes an x-ray controller 28 that provides power and timing signals to x-ray source 14, and a gantry motor controller 30 that controls a rotational speed and position of gantry 12. In some embodiments, gantry motor controller 30 may control a tilt angle of gantry 12. A data acquisition system (DAS) 32 in control mechanism 26 samples and digitizes the projection data from detector elements 20 and converts the projection data to sampled and digitized projection data for subsequent processing. In some embodiments, DAS 32 may be positioned adjacent to detector array 18 on gantry 12, as depicted.

Pre-processor 33 receives the sampled and digitized projection data from DAS 32 to pre-process the sampled and digitized projection data. In one embodiment, pre-processing includes, but is not limited to, an offset correction, a primary speed correction, a reference channel correction, an air-calibration, and/or applying a negative logarithmic operation. As used herein, the term processor is not limited to just those integrated circuits referred to in the art as a processor, but broadly refers to a controller, a microcontroller, a microcomputer, a programmable logic controller, an application specific integrated circuit, and any other programmable circuit, and these terms are used interchangeably herein. Pre-processor 33 pre-processes the sampled and digitized projection data to generate pre-processed projection data.

An image reconstructor 34 receives the pre-processed projection data from pre-processor 33 and performs image reconstruction, such as filtered back-projection (FBP), to generate a reconstructed image. The reconstructed image is applied as an input to a computer 36 which stores the reconstructed image in a mass storage device 38, where the mass storage device 38 may include, as non-limiting examples, a hard disk drive, a floppy disk drive, a compact disk-read/write (CD-R/W) drive, a Digital Versatile Disc (DVD) drive, a flash drive, and/or a solid-state storage device. As used herein, the term computer is not limited to just those integrated circuits referred to in the art as a computer, but broadly refers to a processor, a microcontroller, a microcomputer, a programmable logic controller, an application specific integrated circuit, and any other programmable circuit, and these terms are used interchangeably herein. An x-ray controller 28 adjusts a tube current within x-ray source 14 based on a quality of the reconstructed image.

Computer 36 also receives commands and scanning parameters from a user, such as an operator, via a console 40 that includes a user interface device, such as a keyboard, mouse, voice-activated controller, touchscreen or any other suitable input apparatus. An associated display 42 allows a user, such as an operator, to observe the reconstructed image and other data from computer 36. The commands and scanning parameters are used by computer 36 to provide control signals and information to DAS 32, x-ray controller 28, and gantry motor controller 30. In addition, computer 36 operates a table motor controller 44 which controls a motorized table 46 to position subject 22 within gantry 12. Particularly, table motor controller 44 adjusts motorized table 46 to move portions of subject 22 and center the subject 22 in a gantry opening 48. In some examples, the gantry 12 may be motorized and the motorized table 46 may be fixed. In some more examples, multiple gantries may be used.

In an alternative embodiment, a high frequency electromagnetic energy projection source configured to project high frequency electromagnetic energy toward subject 22 may be used instead of x-ray source 14. A detector array disposed within a gantry and configured to detect the high frequency electromagnetic energy may also be used instead of detector array 18.

In one embodiment, the image reconstructor 34 stores the reconstructed images in the mass storage device 38. Alternatively, the image reconstructor 34 transmits the reconstructed images to the computer 36 for generating useful patient information for diagnosis and evaluation. In certain embodiments, the computer 36 transmits the reconstructed images and/or the patient information to a display 42 communicatively coupled to the computer 36 and/or the image reconstructor 34. In some embodiments, patient information may be collected from an external source, possibly electronically (Electronic Medical Record) and may also be entered by the operator of the machine.

In one embodiment, the display 42 allows the operator to evaluate the imaged anatomy. The display 42 may also allow the operator to select a volume of interest (VOI) and/or request patient information, for example, via graphical user interface (GUI) for a subsequent scan or processing.

In one embodiment, an optional sensor 52 may track the position of the subject 22 during data acquisition. As such, sensor 52 may comprise one or more sensors positioned on the gantry 12. As another example, sensor 52 may comprise a range sensor positioned on the gantry 12, for example on the detector array 18 and/or the x-ray source 14, and configured to sense a distance of the subject 22 from the sensor 52. Optional sensor 52 may communicate a sensed position of the subject 22 to the computer 36, the pre-processor 33, and/or the image reconstructor 34. As described further herein with regard to FIG. 3, the sensed position of the subject 22 during a scan may subsequently be used to determine a shape and size of the subject 22, which in turn may be used to determine if a collision is likely to occur between the subject 22 and the imaging system when the subject 22 is in an off-center position.

Figure 2:
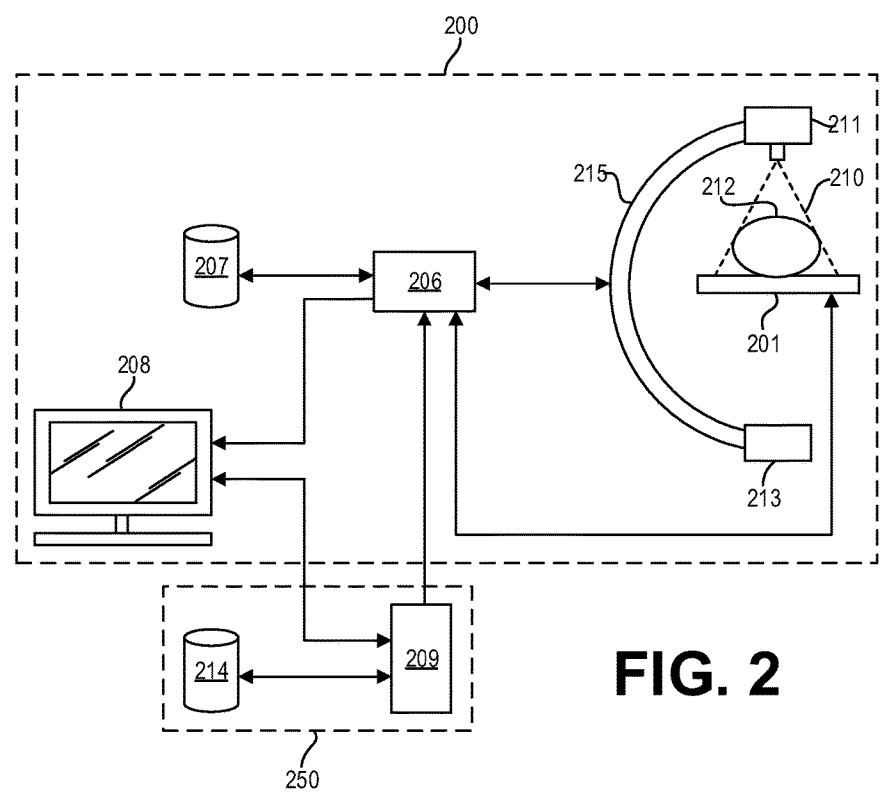
FIG. 2 is a block schematic diagram of a CT system including a C-arm assembly according to an embodiment of the invention.

FIG. 2 schematically illustrates a medical imaging system 200 to acquire 2D projection images for the reconstruction of a 3D image of an object such as an organ. The medical imaging system 200 comprises a support 201 intended to receive a patient 212 to be examined, in whom it is desired to image an organ (not depicted); a source 211 intended to emit an x-ray beam 210; a detector 213 arranged facing the source 211 and configured to detect the x-rays emitted by the source 211; a control unit 206; a storage unit 207; and a display unit 208. The x-ray source 211 and the detector 213 are connected by means of a C-arm 215, for example.

The detector 213 may be a semiconductor image sensor, for example comprising caesium iodide phosphor (scintillator) on a transistor/amorphous silicon photodiode array. Other suitable detectors may include a CCD sensor or a direct digital detector which directly converts x-rays into digital signals. The detector 213 illustrated in FIG. 2 is planar and defines a planar image surface, however, other geometries are evidently also suitable. The control unit 206 is used to control an acquisition by setting several parameters such as the radiation dose to be emitted by the x-ray source 211 and the positioning of the source 211 and detector 213. It is connected to the C-arm 215 via a wired or wireless connection.

The storage unit 207 is connected to the control unit 206 to record parameters and acquired images. It is possible to place the storage unit 207 either inside or outside the control unit 206. The storage unit 207 may be formed of a hard disk or solid state drive (SSD), or any other removable, re-writeable storage means (USB keys, memory cards, and so on). The storage unit 207 may comprise a ROM/RAM memory of the control unit 206, a USB key, memory card, or memory of a central server.

The display unit 208 is connected to the control unit 206 to display acquired images and/or information on acquisition control parameters. For example, the display unit 208 may be a computer screen, a monitor, flat screen, plasma screen, or any other type of display device. The display unit 208 allows the practitioner to control the reconstruction and/or display of acquired 2D images.

The medical imaging system 200 is coupled with a processing system 250. The processing system 250 comprises a computing unit 209 and a storage unit 214. The processing system 250 receives acquired images stored in the storage unit 207 of the medical imaging system 200 from which it performs a certain number of processing operations, e.g., a reconstruction of a 3D image from 2D images. The transmission of data from the storage unit 207 of the medical imaging system 200 towards the computing unit 209 of the processing system 250 may take place via an internal or external computer network or using any suitable physical memory medium, e.g., diskettes, CD-ROM, DVD-ROM, external hard disk, USB key, SD card, and so on.

The computing unit 209 comprises one or more computers, for example, or one or more processors, one or more microcontrollers, one or more microcomputers, one or more programmable logic controllers, one or more application-specific integrated circuits, other programmable circuits, or other devices which include a computer such as a workstation. In addition, the processing system 250 comprises a storage unit 214 to store data generated by the computing unit 209.

The computing unit 209 may be connected to the display unit 208 as depicted or to another display (not shown). In addition, the processing system 250 may be included in the medical imaging system 200. In such an example, the storage units 207, 214 may comprise a single storage unit and similarly the computing units 206, 209 may comprise a single computing unit.

During a diagnostic scan, using a cone beam computed tomography scan systems for example, the user or operator frequently encounters issues with positioning the anatomy of interest within the field of view while ensuring that there is no collision with the patient and or the table on which the patient is resting, during the rotational acquisition of the scan. The operator typically uses trial and error method, leading to longer operation time as well as a sub-optimal X-ray dose (and additional contrast in the case of vascular interventions). More automated methods for positioning the patient inside a CBCT system are desired.

Figure 3:
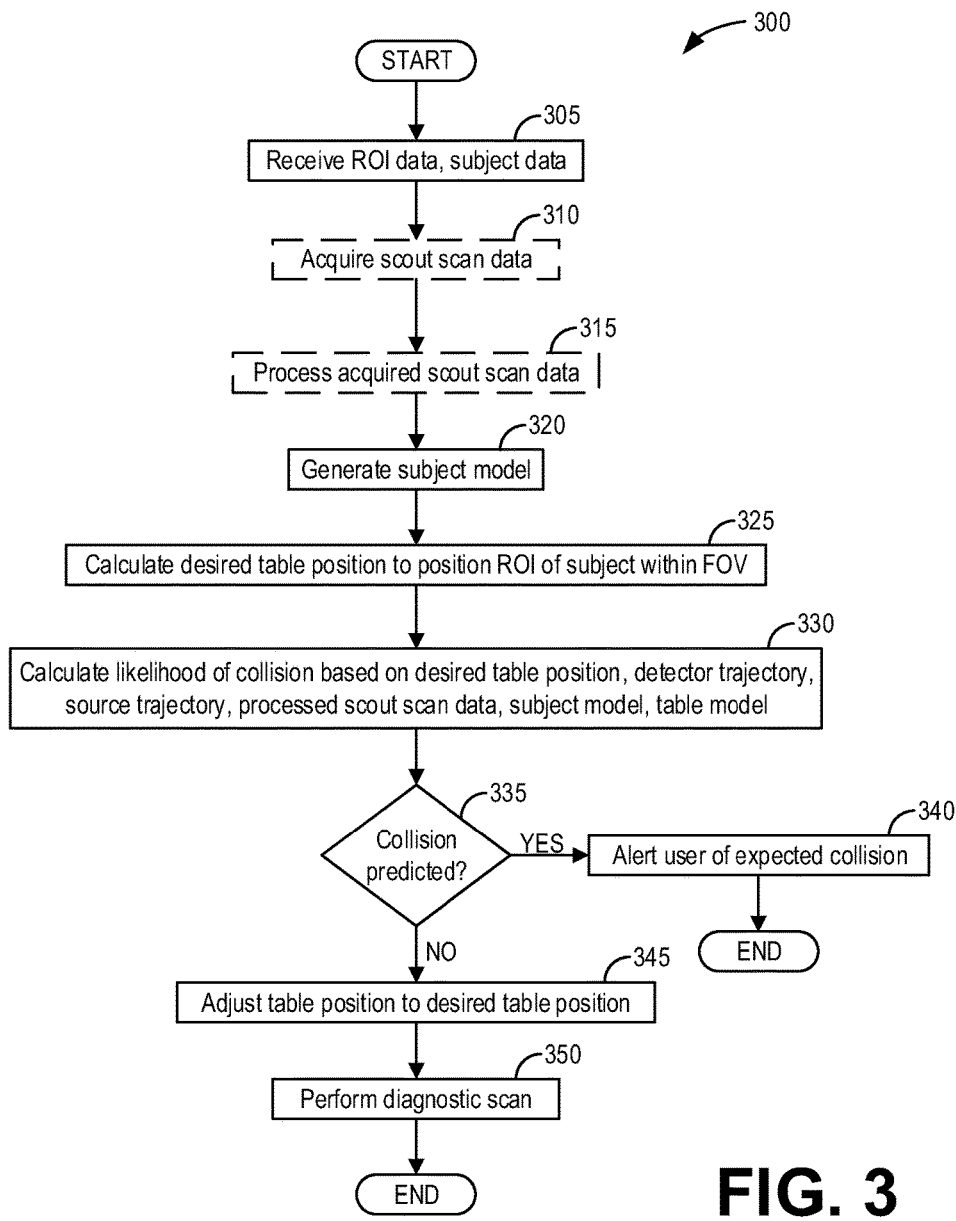
FIG. 3 shows a high-level flow chart illustrating an example method for collision avoidance in cone beam computed tomography according to an embodiment of the invention.

FIG. 3 shows a high-level flow chart illustrating an example method 300 for collision avoidance in cone beam computed tomography according to an embodiment of the invention. In particular, method 300 relates to estimating a table position during a diagnostic scan using an imaging system such as a CBCT system, and adjusting the table position during image acquisition based on a prediction for collision of the table with the imaging system. Method 300 may be described with regard to the components and systems depicted in FIGS. 1 and 2, however it should be appreciated that the method may be applied to other systems without departing from the scope of the present disclosure. For example, method 300 may be carried out by a processor, including but not limited to one or more of pre-processor 33, image reconstructor 34, computer 36, control unit 206, and/or computing unit 209, and may be stored as executable instructions in non-transitory memory, such as mass storage 38, storage unit 207, and/or storage unit 214.

Method 300 may begin at 305. At 305, method 300 includes receiving region of interest (ROI) data and patient data. The ROI data may comprise a specified organ or anatomy or region to be imaged. Subject or patient data may comprise, as non-limiting examples, data such as height and weight of the patient.

At 310, method 300 may optionally include acquiring scout scan data. Acquiring scout scan data comprises performing a scout scan comprising a preliminary scan with a reduced dosage. During a scout scan, the subject may be positioned in the center of the imaging plane such that no collision between the imaging system and the subject is expected. As such, the patient shape may be estimated using one or multiple fluoroscopic exposures in which the photon absorption may provide an estimate on the patient thickness for this incidence. Multiple incidences may further refine the patient shape estimation, for example. In some examples, a 90° rotation may be used to estimate the thickness of the patient and use a symmetry assumption to further guess the patient shape. The position of the center of this shape may be provided by the table with the use of priori information (e.g. assuming that the patient is off-centered laterally on the table by a given distance). In some more examples, scout scan data may be acquired on a different imaging device than the current system. An example would be data from an MRI or CT which may allow to visualize the skin line because the field of view is not truncated on these machines.

For example, FIG. 4 shows a diagrammatical view 400 of example source and detector trajectories with respect to a subject 401 centered in the imaging plane. In particular, the detector trajectory 410 shows the position of the detector during a rotation, while the source trajectory 415 shows the position of the x-ray source during the rotation. The trajectories 410 and 415 define an isocenter located at $(x_1, y_1)$ with an FOV 420 centered on the isocenter. As discussed above, the subject 401 and table 403 may be centered on the isocenter such that the center of the table 403 coincides with the horizontal position $x_1$. As shown, there is no collision between the imaging system (i.e., the detector and the x-ray source) and the subject.

Referring again to FIG. 3, in some examples a position sensor, such as sensor 52 described herein above with regard to FIG. 1, may be attached to the detector assembly and/or the x-ray source. During the scout scan, the position sensor may sense the distance from the detector and/or the source to the subject. As such, when the position sensor is used, the scout scan may be a potentially radiation-free scout scan, for example.

If the scout scan is performed at 310, then method 300 proceeds to 315. At 315, method 300 may optionally include processing the acquired scout scan data. Processing the acquired scout scan data may comprise reconstructing one or more images from the acquired scout scan data to determine the location of the ROI within the subject. For example, the shape may be represented as an image, an equation, a list of points, etc.

Continuing at 320, method 300 includes generating a subject model, or a model of the subject containing estimates of the shape and size of the subject. For example, the reconstructed images obtained at 315 may be used to create a model of the subject which includes the shape and size of the subject. In such an example, the skin of the subject may be detected in the reconstructed images to create the model. For example, the skin of the subject may be detected by a body wide CT scan. Additionally or alternatively, in examples including a position sensor, a patient model may be created based on the sensed distance from the detector and/or source to the subject obtained at 310.

In some embodiments, actions 310 and 315 may not be performed, and so alternative techniques for estimating the shape and size of the subject may be used. For example, a subject model may be created for a human subject based on the body mass index (BMI) of the subject. The BMI may be calculated based on the subject data received at 305, such as the height and weight of the subject. As another example, x-ray attenuation from prior fluoroscopic images can be used to estimate the patient thickness.

After creating the subject model, method 300 proceeds to 325, method 300 includes calculating a desired table position to position the ROI of the subject within the FOV of the imaging system. As a non-limiting example, the desired table position may be calculated based on one or more of a detector trajectory, a source trajectory, the processed scout scan data, the subject model, and a table model. For example, if a scout scan was performed at 310 and the location of the ROI is determined at 315, then the desired table position is calculated such that the location of the ROI coincides with the FOV of the imaging system. As another example, the location of the ROI may be estimated based, for example, on an atlas or prior knowledge of the operator of the imaging system.

At 330, method 300 includes calculating the likelihood of a collision between the imaging system (e.g., the detector and/or the x-ray source), and the table and/or the subject. The likelihood of a collision may be calculated based on, as non-limiting examples, one or more of the desired table position, the detector trajectory, the source trajectory, the processed scout scan data, the subject model (e.g., the shape and size of the subject), and the table model (e.g., the shape and size of the table). The table model is known a priori, as the shape and size of the table typically does not change after the table is manufactured. In examples where multiple different table shapes are used on the same system, different models may be embedded and the table shape may be selected based on based on a sensor/device (e.g., RFID) to identify the table model being currently used.

For example, FIG. 5 shows a diagrammatic view 500 of example detector and source trajectories with respect to an off-center subject 501 wherein no collision is expected. In particular, the detector trajectory 510 shows the position of the detector during a rotation, and the source trajectory 515 shows the position of the source during a rotation. The subject 501 and the table 503 are centered at a horizontal position $x_2$ away from the horizontal isocenter position $x_1$. An ROI of the subject 501 is positioned within the FOV 520. In this example, calculating the likelihood of a collision comprises checking that the detector trajectory 510 and the source trajectory 515 do not overlap with the subject 501 or the table 503 when the table 503 is positioned at $x_2$.

In contrast, FIG. 6 shows a diagrammatic view 600 of example detector and source trajectories with respect to an off-center subject 601 wherein a collision is expected. Here, the ROI of the subject 601 is positioned within the FOV 620, but the size of the subject 601 is larger than the size of the subject 501 discussed above. As a result, the center of the table 603 is located at a horizontal position $x_3$, which is a greater distance from the horizontal isocenter position $x_1$ than the position $x_2$ of the table 503 in FIG. 5. The detector trajectory 610 and the source trajectory 615 thus coincide with both the subject 601 and the table 603. In this example, a collision is expected due to the coincidence of the trajectories with the subject and table positions.

Referring again to FIG. 3, after calculating the likelihood of a collision, method 300 proceeds to 335. At 335, method 300 includes determining if a collision is predicted. A collision is predicted if the calculation at 330 indicates that the detector and/or source trajectories coincide with a position of the table and/or the subject during a rotation of the detector and the source. In some examples, collision may be predicted, if the likelihood of collision is higher than a threshold, the threshold may be based on an extent of overlap or coincidence of the trajectories with the subject and table positions. In such examples, collision may not be predicted if the likelihood of collision is lower than the threshold.

If a collision is predicted ("YES"), method 300 proceeds to 340. At 340, method 300 includes alerting a user of the imaging system of the expected collision. Alerting the user of the expected collision may comprise, as a non-limiting example, displaying a visual alert to the user via the display device 42 depicted in FIG. 1 or the display 208 depicted in FIG. 2. The visual alert may comprise, as an example, a red circle indicating that a scan should not be performed. Similarly, if a collision is not predicted, a green circle may be displayed indicating that no collision is expected and a scan may be performed. A diagnostic scan may not be performed until the user takes action to avoid the collision. Method 300 then ends.

Returning to 335, if a collision is not predicted ("NO"), method 300 proceeds to 345. At 345, method 300 includes adjusting the table position to the desired table position calculated at 320. As mentioned above, a green circle may also be displayed to the user to indicate that no collision is expected. Continuing at 350, method 300 includes performing a diagnostic scan of the subject. Method 300 may then end.

In this way, diagnostic images of the ROI can be obtained without collision of the imaging system with the subject. Furthermore, the operator of the imaging system can avoid performing a trial-and-error process to correctly position the subject within the imaging plane, during which the subject may receive a radiation dose when the ROI is outside the FOV.

Figure 7:
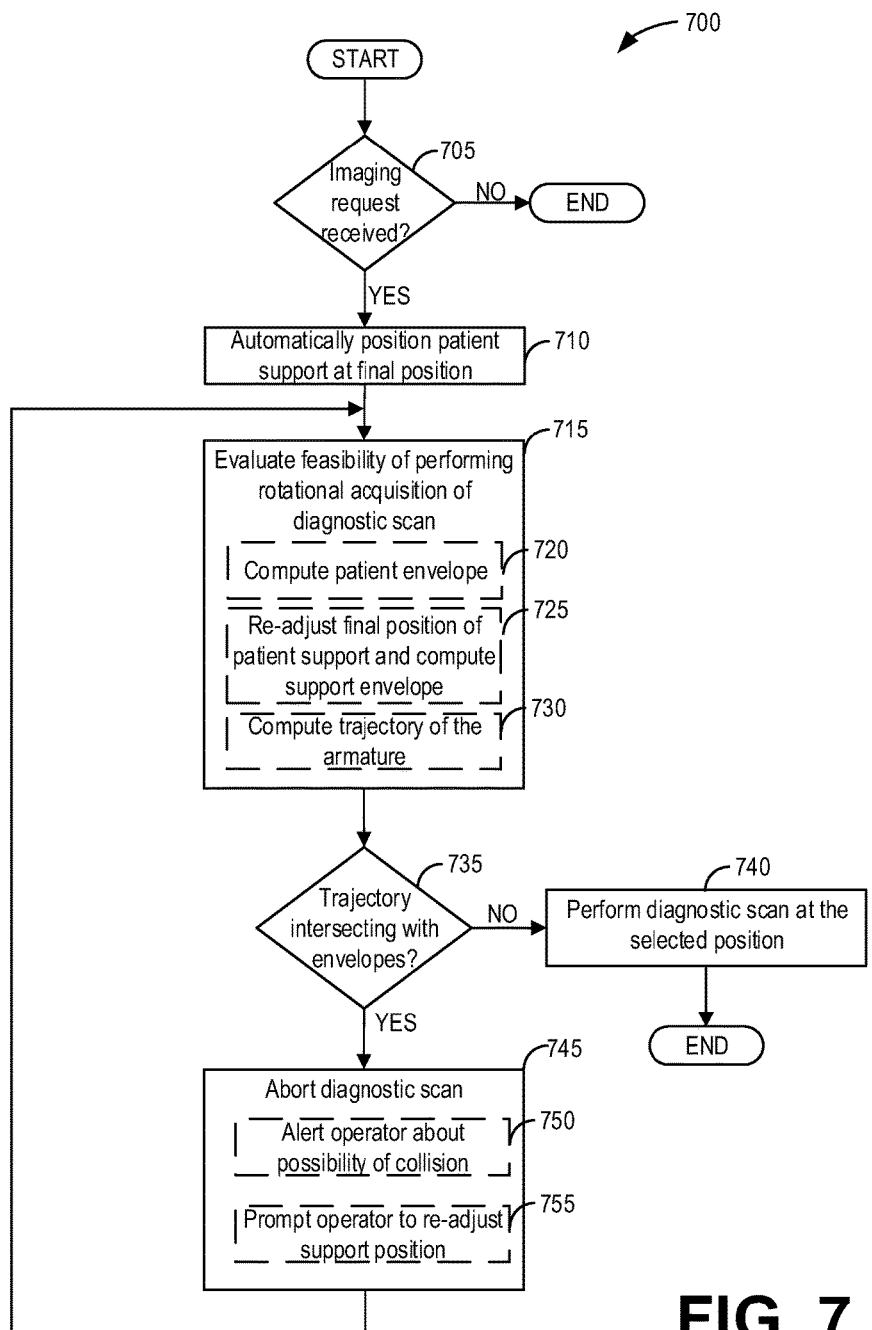
FIG. 7 shows a high-level flow chart illustrating an example method for automatically adjusting the position of a patient support according to an embodiment of the invention.

FIG. 7 shows a high-level flow chart illustrating an example method 700 for automatically adjusting the position of the patient support according to an embodiment of the invention. Specifically method 700 relates to determining whether a table position is suitable for performing diagnostic scan using an imaging, without any chance of collision between the imaging system and one or more of the table and the patient.

At 705, method 700 includes determining if an imaging request is received. Imaging request may include request from an operator to perform a diagnostic scan on a patient and may additionally and alternatively include details on the anatomy of interest. If no request is received at 705, then method ends.

However, if the imaging request is received at 705, then method 700 proceeds to 710, where the patient support or table is automatically moved to a final position. Herein, the patient rests on the patient support or table, and the final position is determined such that the anatomy of interest is positioned within the field of view. In cone beam CT, the field of view (FOV) of the imaging system is small and centered on the isocenter, for example. In one example, the final position of the support may be determined by solving three-dimensional equations of motion. The processor may be able to adaptively solve the equations of motion to determine the final position of the support. In some embodiments, the values such as length of support, height of support, current position of the support, shape of the support, and so on may be included in a look-up table, and subsequently used solve the equations of motion to determine the final position of the table and further update the look-up table, which the processor can then look-up for example. In some examples, the final position of the patient support may further adjusted based on the anatomy of interest to be imaged. In some examples, the final support position may be coarse position adjustment of the support that may be further fine-tuned later as described below.

Once the patient support final position is determined, the support may be automatically moved to the final position at 710. Then, method 700 proceeds to 715, where feasibility of performing rotational acquisition of the diagnostic scan may be evaluated. Evaluating the feasibility of performing the diagnostic scan may additionally or alternatively involve computing patient envelope and support envelope at 720. As such, the patient envelope may include information about the shape and size of the patient. The patient envelope may be determined based on a patient model further based on one or more of body mass index of the patient, skin of the patient determined using prior images, and output of sensors embedded in the imaging system. For example, the patient envelope may be generated by using any previous scans or images. In such an example, the skin of the subject may be detected in the reconstructed images to create the patient envelope. Additionally or alternatively, in examples including a position sensor as described earlier, a patient envelope may be created based on the sensed distance from the detector and/or source to the subject.

Additionally or alternatively, in some examples, the final position of the support may be re-adjusted based on the patient envelope at 725. In addition, the support envelope may be computed at 725. For example, if the anatomy of interest is the right part of the right liver, the support position may be further fine-tuned based on the size, weight and height of the patient, for example. In one example, the support envelope may include circumference and/or contours of the support. In some examples, the patient envelope may be displayed on a display.

Furthermore, at 730, the trajectory of the armature may be computed. For example, the armature may include both the source and detector coupled and may be capable to rotational movement around the patient and/or the patient support. The trajectory of the armature may include trajectories of both the source and the detector, for example. The trajectory of the armature around the patient and/or the patient support, particularly around the anatomy of interest may be computed by determining the path of the armature around the anatomy of interest. In some examples, the trajectory of the armature may be displayed on the display.

Subsequently, method 700 proceeds to 735, where it may be determined if the trajectory of the armature is intersecting with the patient and support envelopes. Determining if the trajectory is intersecting with the patient envelope and/or support envelope may determine the likelihood of a collision of the armature with one or more of the patient and/or the patient support, for example. In the example where the trajectory and the envelopes are displayed on a display, any intersection between the trajectory armature with one or more of the patient envelope and support envelope may be determined if any of the displayed trajectory and envelopes intersect on the display.

As such, the likelihood of collision is higher when trajectory of the armature intersects with the envelope of the support and/or the patient envelope and the likelihood of collision is lower when the trajectory of the armature does not intersect with the envelope of the support and/or the patient envelope.

If the armature trajectory intersects with one or more of the patient envelope and the support envelope, indicating that the likelihood of collision is higher, then method 700 proceeds to 745 where the scan may be aborted. Furthermore, the operator of the imaging system may be alerted about the possibility of collision at 750. The alert may one or more of an audio alert and a visual alert. Further still, the operator may be prompted to re-adjust the support position to a new position at 755 and method 700 returns back to 715, where the feasibility of performing the rotational acquisition of the diagnostic scan at the new support position may be re-evaluated.

However, if the armature trajectory does not intersect with one or more of the patient envelope and the support envelope, indicating that the likelihood of collision is lower, then method 700 proceeds to 740, where the diagnostic scan may be performed at the selected position (e.g., final position) and the method ends. In this way, diagnostic scans may be performed without collision of the imaging system with one or more of the patient and the patient support. Furthermore, the operator of the imaging system can selectively perform the scan when there is no likelihood of collision, thereby avoiding any trial-and-error adjustment process to position the patient within the imaging plane, and thereby avoiding any unwanted radiation exposure.

A technical effect of this disclosure calculating the likelihood of a collision between the imaging system and one or more of the subject and the subject support. The technical effect of computing the likelihood of collision, is that the support position may be automatically adjusted to the position wherein the likelihood of collision is lower and the scan may be performed at the selected position. In addition, the entire adjustment procedure is further automated with minimal user intervention.

The systems and methods described above provide for a method for an imaging apparatus, the method comprising calculating a likelihood of a collision between the imaging apparatus and one or more of a subject and a subject support based on a model of the subject, performing a scan of the subject responsive to the likelihood below a threshold, and not performing the scan otherwise.

In a first example, the method may additionally or alternatively include wherein the likelihood of the collision is calculated based on a shape and size of the subject and a trajectory of a source and a detector of the imaging apparatus. A second example of the method optionally includes the first example and further includes calculating the model of the subject based on one or more of a height of the subject and a weight of the subject. A third example of the method optionally includes one or more of the first and the second examples, and further includes calculating the model of the subject based on one or more of prior image reconstructions and fluoroscopic exposures. A fourth example of the method optionally includes one or more of the first through the third examples, and further includes calculating the model of the subject based on a position of the subject sensed by a sensor coupled to the imaging apparatus. A fifth example of the method optionally includes one or more of the first through the fourth examples, and further includes calculating a position of the subject support upon which the subject rests, such that a region of interest (ROI) of the subject coincides with a field of view (FOV) of the imaging apparatus. A sixth example of the method optionally includes one or more of the first through the fifth example, and further includes wherein calculating the likelihood of the collision is further based on the position of the subject support. In another representation, as a seventh example of the method, the method may optionally include one or more of the first through the sixth example, and further include wherein the patient thickness may be determined based on one or more of fluoroscopic exposures and further based on x-ray absorption.

The systems and methods described above also provide for an imaging system, the imaging system comprising a gantry, a source coupled to the gantry and configured to generate energy, a detector coupled to the gantry opposite the source and configured to detect the energy, a patient support positioned between the source and the detector; and a processor communicatively coupled to the gantry, the source, the detector, and the patient support, the processor configured with instructions in non-transitory memory that when executed cause the processor to calculate a position of the patient support such that a region of interest of a subject resting on the patient support coincides with a field of view between the source and the detector, calculate a likelihood of a collision of the source and the detector with the subject and/or the patient support if the patient support is positioned at the calculated position, and responsive to the likelihood of the collision being below a threshold, adjust the patient support to the calculated position and perform a scan of the subject. In a first example of the imaging system, the imaging system may additionally or alternatively include wherein the likelihood of collision is calculated based on one or more of a shape, size, and weight of the subject and a trajectory of the source and the detector of the imaging system. A second example of the imaging system optionally includes the first example and further includes wherein the threshold is based on an extent of overlap between the trajectory of the source and the detector with the patient support and/or a subject envelope. A third example of the system optionally includes one or more of the first and the second examples and further includes wherein the subject envelope is based on one or more of a prior image reconstruction, a patient model, and sensor output. A fourth example of the system optionally includes one or more of the first through the third examples, and further includes responsive to the likelihood of the collision being above the threshold, not perform the scan at the position, recalculate a new position of the patient support, and re-evaluate likelihood of collision at the new position.

The systems and methods described above also provide for a method comprising receiving a request to image an anatomy of a patient, automatically positioning the patient on a support at a position determined based on one or more of a patient envelope and the anatomy of the patient and evaluating feasibility of performing a rotational acquisition of a scan using an imaging system on the patient by computing a likelihood of collision between the imaging system and one or more of the support and the patient. In a first example of the method, the method may additionally or alternatively include wherein the patient envelope is determined based on a patient model based on one or more of a weight of the patient, a height of the patient, a body mass index of the patient, and a thickness of the patient determined using prior images, and output of sensors embedded in the imaging system. A second example of the method optionally includes the first example, and further includes wherein the imaging system includes a detector and a source mounted on an armature of the imaging system. A third example of the method optionally includes one or more of the first and the second examples, and further includes wherein the likelihood of collision is higher when trajectory of the armature intersects with an envelope of the support and/or the patient envelope. A fourth example of the method optionally includes one or more of the first through the third examples, and further includes wherein the likelihood of collision is lower when the trajectory of the armature does not intersect with the envelope of the support and/or the patient envelope. A fifth example of the method optionally includes one or more of the first through the fourth examples, and further includes performing the scan when the likelihood of collision is lower than a threshold at the position of the support of the patient. A sixth example of the method optionally includes one or more of the first through the fifth example, and further includes one or more of aborting the scan and alerting an operator of the imaging system about a possibility of collision when the likelihood of collision is higher than a threshold. A seventh example of the method optionally includes one or more of the first through the sixth examples, and further includes prompting the operator to re-adjust position of the support to a new position, and re-evaluate feasibility of performing the scan at the new position.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an imaging apparatus, comprising:
   calculating a likelihood of a collision between the imaging apparatus and one or more of a subject and a subject support based on a model of the subject;
   performing a scan of the subject responsive to the likelihood below a threshold; and
   not performing the scan otherwise.

2. The method of claim 1, further comprising calculating the likelihood of the collision based on a shape and a size of the subject and a trajectory of a source and a detector of the imaging apparatus.

3. The method of claim 1, further comprising calculating the model of the subject based on one or more of a height of the subject and a weight of the subject.

4. The method of claim 1, further comprising calculating the model of the subject based on one or more of prior image reconstructions and fluoroscopic exposures.

5. The method of claim 1, further comprising calculating the model of the subject based on a position of the subject sensed by a sensor coupled to the imaging apparatus.

6. The method of claim 1, further comprising calculating a position of the subject support upon which the subject rests, such that a region of interest (ROI) of the subject coincides with a field of view (FOV) of the imaging apparatus.

7. The method of claim 6, wherein calculating the likelihood of the collision is further based on the position of the subject support.

8. An imaging system, comprising:
   a gantry;
   a source coupled to the gantry and configured to generate energy;
   a detector coupled to the gantry opposite the source and configured to detect the energy;
   a patient support positioned between the source and the detector; and
   a processor communicatively coupled to the gantry, the source, the detector, and the patient support, the processor configured with instructions in non-transitory memory that, when executed, cause the processor to:
      calculate a position of the patient support such that a region of interest of a subject resting on the patient support coincides with a field of view between the source and the detector;
      calculate a likelihood of a collision of the source and the detector with the subject and the patient support if the patient support is positioned at the calculated position; and
      responsive to the likelihood of the collision being below a threshold, adjust the patient support to the calculated position.

9. The imaging system of claim 8, wherein the processor is further configured with instructions in non-transitory memory that, when executed, cause the processor to calculate the likelihood of the collision based on one or more of a shape, a size, and a weight of the subject and a trajectory of the source and the detector of the imaging system.

10. The imaging system of claim 9, wherein the threshold is based on an extent of overlap between the trajectory of the source and the detector with the patient support and/or a subject envelope.

11. The imaging system of claim 10, wherein the subject envelope is based on one or more of a prior image reconstruction, a fluoroscopic image, or sensor output.

12. The imaging system of claim 8, wherein the processor is further configured with instructions in non-transitory memory that, when executed, cause the processor to:
   re-calculate a new position of the patient support; and
   re-evaluate the likelihood of the collision at the new position, responsive to the likelihood of the collision being above the threshold.

13. A method, comprising:
   receiving a request to image an anatomy of a patient;
   automatically positioning the patient on a support at a position determined based on one or more of a patient envelope and the anatomy of the patient; and
   evaluating a feasibility of performing a rotational acquisition of a scan using an imaging system on the patient by computing a likelihood of collision between the imaging system and one or more of the support and the patient.

14. The method of claim 13, further comprising determining the patient envelope based on a patient model further based on one or more of a height of the patient, a weight of the patient, body mass index of the patient, and a thickness of the patient determined using one or more of prior images and output of sensors embedded in the imaging system.

15. The method of claim 13, wherein the imaging system includes a detector and a source mounted on an armature of the imaging system.

16. The method of claim 15, wherein computing the likelihood of collision between the imaging system and one or more of the support and the patient comprises computing a higher likelihood of collision when a trajectory of the armature intersects with an envelope of the support and/or the patient envelope.

17. The method of claim 16, wherein computing the likelihood of collision between the imaging system and one or more of the support and the patient comprises computing a lower likelihood of collision when the trajectory of the armature does not intersect with the envelope of the support and/or the patient envelope.

18. The method of claim 17, further comprising performing the scan when the likelihood of collision is lower than a threshold at the position of the support of the patient.

19. The method of claim 15, further comprising one or more of aborting the scan and alerting an operator of the imaging system about a possibility of collision when the likelihood of collision is higher than a threshold.

20. The method of claim 19, further comprising prompting the operator to re-adjust the position of the support to a new position, and re-evaluate the feasibility of performing the scan at the new position.

\* \* \* \* \*